United States Patent [19]
Narciso, Jr. et al.

[11] Patent Number: 5,231,684
[45] Date of Patent: Jul. 27, 1993

[54] OPTICAL FIBER MICROLENS

[75] Inventors: Hugh L. Narciso, Jr., Santa Barbara; Daniel R. Doiron, Santa Ynez, both of Calif.

[73] Assignee: PDT Systems, Goleta, Calif.

[21] Appl. No.: 902,674

[22] Filed: Jun. 22, 1992

[51] Int. Cl.$^5$ .............................. G02B 6/32
[52] U.S. Cl. .............................. 385/80; 385/33; 385/51; 385/77
[58] Field of Search .................. 385/15, 31, 33, 34, 385/35, 51, 73, 74, 76, 77, 78, 80, 93

[56] References Cited

U.S. PATENT DOCUMENTS

| | | | |
|---|---|---|---|
| 4,281,891 | 8/1981 | Shinohara et al. | 385/33 |
| 4,330,171 | 5/1982 | Malsot et al. | 385/80 |
| 4,378,954 | 4/1983 | Baker | 385/80 |
| 4,440,470 | 4/1984 | Khoe | 385/33 |
| 4,641,912 | 2/1987 | Goldenberg | 385/43 |
| 4,718,055 | 1/1988 | Winzer | 385/33 |
| 4,779,947 | 10/1988 | Ito | 385/33 |
| 4,842,390 | 6/1989 | Sottini et al. | 385/43 |
| 4,913,510 | 4/1990 | Lynch et al. | 385/35 |
| 5,040,862 | 8/1991 | Burton et al. | 385/33 |
| 5,048,912 | 9/1991 | Kunikane et al. | 385/35 |
| 5,066,090 | 11/1991 | Mayerhofer et al. | 385/35 |
| 5,093,877 | 3/1992 | Aita et al. | 385/34 |
| 5,094,518 | 3/1992 | Musk | 385/35 |

FOREIGN PATENT DOCUMENTS

| | | | |
|---|---|---|---|
| 60-162209 | 8/1985 | Japan | 385/35 X |
| 62-293210 | 12/1987 | Japan | 385/35 X |
| WO90/00753 | 1/1990 | PCT Int'l Appl. | 385/35 X |
| 2148536 | 5/1985 | United Kingdom | 385/35 X |

*Primary Examiner*—Brian Healy
*Attorney, Agent, or Firm*—Michael G. Petit

[57] ABSTRACT

A microlens assembly for use with an optical fiber or fiber bundle that requires no crimping or mechanical distortion of the optical fiber. The microlens assembly has a front lens mounting portion and a rear portion. The rear portion is a cylindrical tube which is bonded to the sheath and cladding of the optical fiber or fiber bundle by means of suitable adhesive. The front lens mounting portion which houses the output lens is also tubular, having an inner diameter greater than the outer diameter of the rear portion. The front lens mounting portion is slid over the rear portion until the desired distribution of light emanating from the lens is achieved. The front lens mounting portion is then locked into position by bonding it to the rear portion by means of an appropriate adhesive. The adhesives are stable at high temperature and have an index of refractions suitable for preventing refractive loss of light from the lateral walls of the fiber core. In one embodiment, the cylindrical space in the microlens assembly between the output lens and the tip of the optical fiber or fiber bundle is filled with an optically transparent fluid or elastomer such as silicone. The filling excludes body fluids from entering the microlens assembly.

5 Claims, 2 Drawing Sheets

5,231,684

OPTICAL FIBER MICROLENS

BACKGROUND OF THE INVENTION

1. Field of the Invention

This invention relates to optical fibers, and more particularly to lenses for the distribution and delivery of light emerging from an optical fiber.

2. Prior Art

Lenses are often applied in the medical field to focus light, typically from a laser source, onto a treatment site. When fiber optics are employed, microlenses are used as the focusing device due to their size and availability. The microlens is attached to the treatment end of the optical fiber to distribute the light from the fiber into a desired pattern or intensity distribution. For applications requiring insertion of the treatment end into the body such as photodynamic therapy (PDT), laser angioplasty, laser lithotripsy, laser surgery, etc., a svelte, low profile delivery device is needed. The device must be safe, easily inserted into the body, capable of delivering substantial power and produce a desired output.

Optically transmissive fibers for transmitting light energy to a remote location from a source are well known in the surgical literature. For example, Sottini, et al., in U.S. Pat. No. 4,842,390, describe a fiber optic device for transmission of laser energy into a blood vessel for angioplasty. Such lenses are useful for either focusing or diverging the light as it emanates from the tip of the optical fiber. Goldenberg, in U.S. Pat. No. 4,641,912 uses a focusing tip on an optical fiber which receives its input light from an excimer laser for producing a high intensity, ultrathin beam of light. All such medically useful optical fibers normally comprise a fiber element having a proximal end and a distal or treatment end. The optical fiber element is adapted to conduct radiation, usually from lasers, from the proximal end of the optical fiber to be emitted at the distal or treatment end. It may also include a microlens secured to the distal end of the optical fiber.

Aita, et al., in U.S. Pat. No. 5,093,877 describe a treatment fiber having a convex lens placed at the treatment end of an optical fiber. The lens is positioned to receive laser radiation emitted from the distal end of the optical fiber and focus it on a treatment site. The lens has two surfaces: a first surface adjacent to, but separated from the distal end of the optical fiber to receive laser radiation from the optical fiber; and a second surface which is substantially convex, positioned to distribute the laser light. The first lens surface is shaped to provide a predetermined distribution pattern from the second lens surface. The assembly, which may be called a microlens also includes a tubular sleeve coupled to the first lens surface. The tubular sleeve is crimped to the optical fiber to hold the distal tip of the fiber core at the focal point of the lens.

While these devices are adequate for some applications, improvements in the design would facilitate the clinical procedures while improving the safety and clinical results. When used internally the potential exists for the lens mounting structure to fail and become detached leaving pieces of the device in the human body.

In summary, the prior art optical fibers for medical treatment utilizing microlenses on the end of an optical fiber have the following shortcomings:

1. They rely on a crimping procedure to secure the lens mounting device to the fiber optic jacket;
2. They produce an output which is not perfectly focused because the crimping procedure distorts the mounting device and therefore its ability to hold the fiber optic and the lens in position relative to each other;
3. They don't have the capacity to handle high-power applications;
4. They couple light out of the fiber inefficiently; and,
5. They do not provide a barrier for biological fluids such as blood. Such fluids can enter the microlens cavity and reduce the efficiency of the microlens.

SUMMARY OF THE INVENTION

An object of this invention is to provide a fiber optic microlens that does not require crimping or induce mechanical distortion of either the lens mounting device or the optical fiber.

It is a further object of this invention to provide a microlens for an optical fiber which is capable of handling high power. That is, it will not overheat when used to deliver the high levels of power required for treatment.

It is yet another object of the invention to provide a microlens for use with an optical fiber that is efficiently coupled to the optical fiber to reduce heating and increase efficiency.

It is still another object of this invention to provide a microlens assembly for use with an optical fiber which exclude biological fluids from contaminating or otherwise entering the microlens assembly during use.

The construction of the microlens assembly for achieving these and other objects of the invention will become apparent if we turn now to the drawings.

DESCRIPTION OF THE PREFERRED EMBODIMENT

Figure 1:
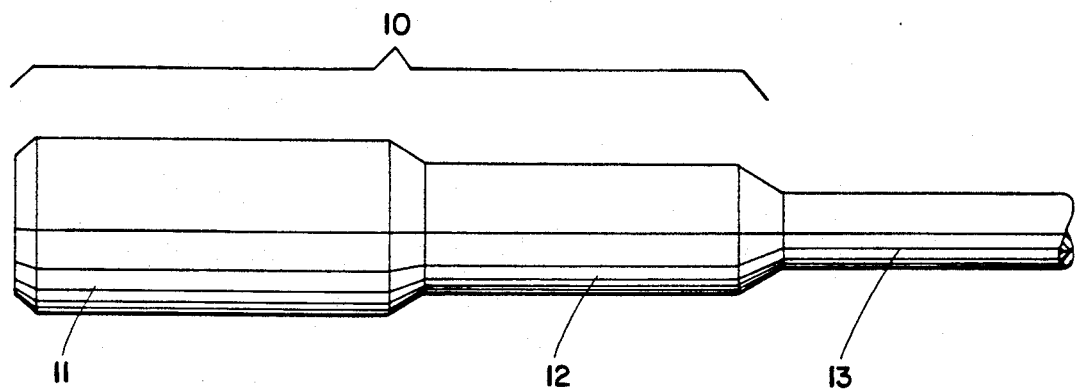
FIG. 1 is a prospective view of the microlens assembly of the present invention affixed to the distal end of an optical fiber.

The microlens delivery system for use with an optical fiber is indicated in FIG. 1 at numeral 10. An optical fiber 13 has at its distal or treatment end a microlens 10 having two parts: a front mounting piece 11, and a rear mounting piece 12.

Figure 2:
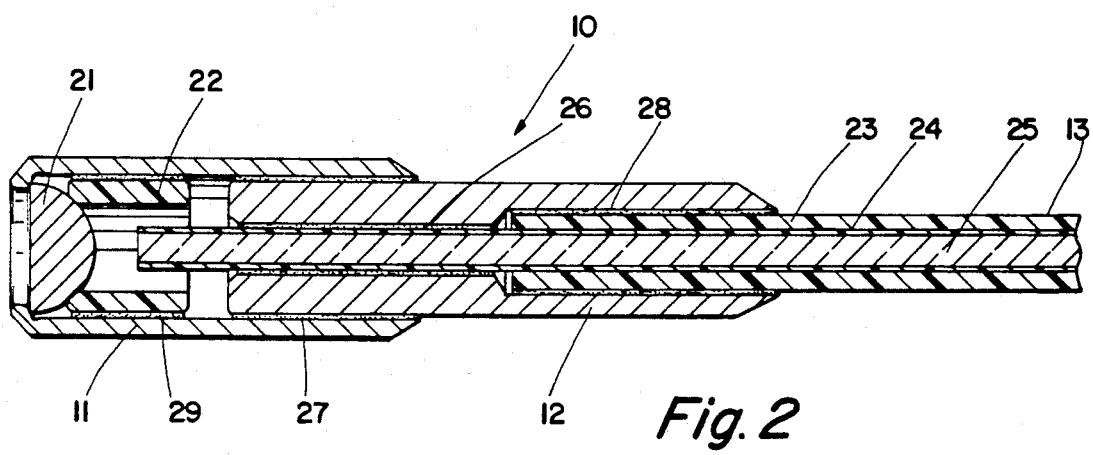
FIG. 2 is a horizontal cutaway view of the improved microlens delivery system of the current invention shown in FIG. 1.

Turning now to FIG. 2, the microlens and the optical treatment fiber 13 are shown in cross section. The optical fiber 13 consists of an optically transmissive core 25 surrounding by a cladding 24 and an outer sheath 23. A portion 25a of the distal treatment end of the optical fiber 13 has the outer sheath 23 stripped away to expose the cladding 24. The rear mounting piece 12, which may be conveniently made from stainless steel, is affixed to the sheath 23 of the optical fiber 13 with a first adhesive 28. The portion 25a of the distal end of the fiber 13 is affixed to the rear mounting piece 12 by means of a second adhesive 26. A convex sapphire lens 21 is held in position within the front mounting piece 11 by means of lens retaining piece 22. The lens retaining piece 22 is attached to the front mounting piece 11 with third adhesive 29. All adhesives are chosen so that they are stable at high temperatures. All (or any two) of the adhesives may be the same. However, it is emphasized that the refractive index of the second adhesive is critical to the efficiency and safety of the device. If an improper refractive index adhesive is used, the light energy will be coupled out of portion 25a of the fiber 13 prior to reaching the tip of the fiber. Coupling the light energy out will reduce the overall efficiency of the device, and more critically, produce heat at the exit point. Such heat could potentially cause the system to fail.

Figure 3:
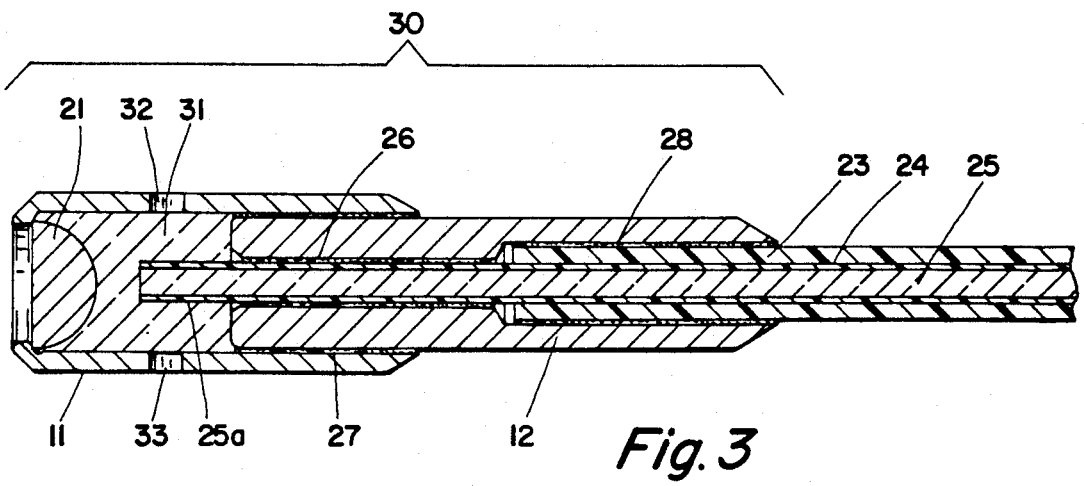
FIG. 3 is a horizontal cross-sectional view of the microlens delivery system of FIG. 1, wherein a coupling fluid is placed between the core of the optical fiber and the lens.

Turning now to FIG. 3, a second preferred embodiment 30 of the microlens is shown. In this embodiment the lens retaining ring 22 is replaced with a silicone plug 31. The microlens 30 is affixed to the fiber as described earlier in FIG. 2, however, the front lens mounting piece has apertures 32 and 33 therein providing fluid communication with the cylindrical interior chamber of the front mounting piece 11. Uncured silicone fluid is introduced through the fluid introduction port 32, and excess fluid leaves through the fluid draining port 33. In the event the fluid is silicone, it can be cured, leaving an optically transparent, solid plug in the cylindrical cavity behind the lens 21, holding the lens 21 securely in position with respect to the distal tip of the optical fiber core 25. The presence of the silicone plug within the front lens mounting piece serves as coupling fluid to efficiently couple light from the fiber optic to the lens with minimal reflection losses and additionally functions by excluding body fluids from entering the microlens mount.

Figure 4:
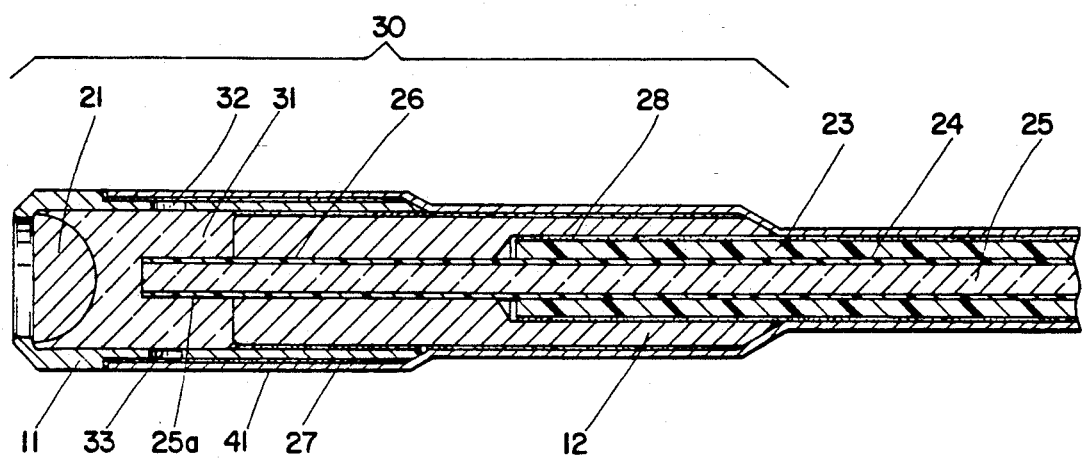
FIG. 4 is yet another horizontal, cross-sectional view of the microlens delivery system of FIG. 3 with a protective sheath surrounding the assembly.

In FIG. 4 a sheath 41 is added to unite and cover the microlens assembly 30 and the optical fiber 13 providing strength and integrity to the assembly. The addition of an outer sheath 41 to the microlens provides a redundant failsafe enclosure.

Figure 5:
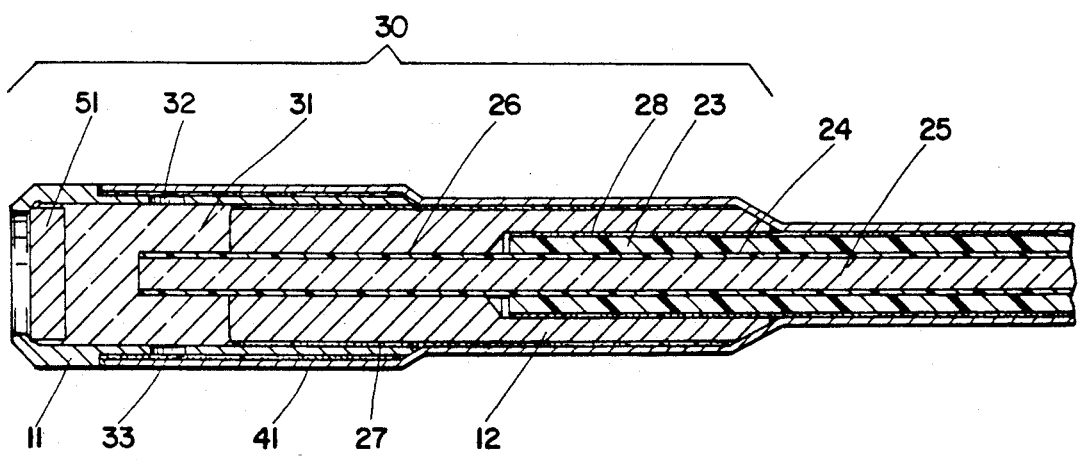
FIG. 5 is a horizontal, cross-sectional view of the microlens delivery system of the present invention with the convex lens of FIGS. 1 through 4 replaced with a flat lens or graded index (GRIN) lens.

FIG. 5 shows a cutaway view of the microlens delivery system with the focusing lens 21 replaced with a flat lens 51. Such a microlens delivery system would be useful for procedures such as laser lithotripsy which does not require a sharp focus, but during which procedures the fiber optic tends to get damaged by the acoustic shock wave produced by the treatment. With a sapphire or diamond flat lens 51 in place to protect the fiber optic tip, laser lithotripsy can continue without having to constantly remove and repair the treatment tip of the treatment fiber. In the case of a graded index (GRIN) lens which is normally flat cylindrical component, the light is bent by layers of varying refractive indices but the lens mount functions as described for FIGS. 1-4.

We have disclosed several embodiments of an improved microlens system for use with an optical fiber and method for construction. It is clear that the microlens assembly described herein is equally applicable to an optical fiber bundle. Various modifications of the present invention will become apparent to those skilled in the art from the foregoing and accompanying drawings. Accordingly, the present invention is to be limited by the scope of the following claims.

What is claimed is:

1. A microlens assembly for the distribution of light energy emanating from the tip of a an optical fiber, said optical fiber comprising an optically transmissive core, a cladding surrounding said core and a outer sheath, said microlens assembly comprising (a) a hollow cylindrical front lens mounting piece having a leading end housing a lens and a trailing end, and (b) a hollow cylindrical rear mounting piece having a leading end securely attached to the cladding of said optical fiber by a first adhesive and trailing end, the trailing end of said rear mounting piece being securely affixed to the outer sheath of said optical fiber by means of a second adhesive and the trailing end of said front lens mounting piece being affixed to the outer surface of the leading end of said rear lens mounting piece by means of a third adhesive.

2. The microlens assembly of claim 1 wherein a cylindrical space is present between the distal end of the optical fiber core and said lens.

3. The microlens assembly of claim 2 wherein said cylindrical space is filled with a fluid having an index of refraction similar to the index of refraction of the optical fiber core and the lens.

4. The microlens assembly of claim 3 wherein said fluid is an uncured optically transmissive elastomer.

5. The microlens assembly of claim 1 wherein said distal end of said optical fiber and said front and rear lens mounting pieces are surrounded by a protective sheath.

* * * * *